United States Patent
Markham et al.

(10) Patent No.: US 9,653,893 B2
(45) Date of Patent: *May 16, 2017

(54) CERAMIC FEEDTHROUGH BRAZED TO AN IMPLANTABLE MEDICAL DEVICE HOUSING

(71) Applicant: HERAEUS DEUTSCHLAND GMBH & CO. KG, Hanau (DE)

(72) Inventors: Jacob Markham, Vadnais Heights, MN (US); Ulrich Hausch, Frankfurt (DE); Goran Pavlovic, Schaafheim (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/991,351

(22) Filed: Jan. 8, 2016

(65) Prior Publication Data
US 2016/0126713 A1    May 5, 2016

Related U.S. Application Data

(62) Division of application No. 13/902,287, filed on May 24, 2013, now Pat. No. 9,431,801.

(51) Int. Cl.
*A61N 1/00* (2006.01)
*H02G 1/00* (2006.01)
(Continued)

(52) U.S. Cl.
CPC .............. *H02G 1/00* (2013.01); *A61N 1/3754* (2013.01); *B23K 1/0056* (2013.01); *H02G 3/22* (2013.01); *Y10T 29/49213* (2015.01)

(58) Field of Classification Search
CPC .......... H02G 1/00; H02G 3/22; A61N 1/3754; B23K 1/0008
See application file for complete search history.

(56) References Cited

U.S. PATENT DOCUMENTS 3,979,187 A    9/1976    Scherer
4,152,540 A    5/1979    Duncan et al.
(Continued)

FOREIGN PATENT DOCUMENTS

DE    69729719    7/2005
DE    102006054249    5/2008
(Continued)

OTHER PUBLICATIONS

Exner, Horst et al., "Laser Joining of Ceramics in Liquid Phase," pp. 1-8 (Nov. 8, 2011).
(Continued)

*Primary Examiner* — Robert N Wieland
(74) *Attorney, Agent, or Firm* — Dicke, Billig & Czaja, PLLC (57) ABSTRACT

One aspect is an implantable medical device with a feedthrough assembly having an insulator and a plurality of conducting elements extending therethrough. The feedthrough assembly is placed in a case with an opening defining a narrow space therebetween. A braze material fills the narrow space, thereby hermetically sealing the feedthrough assembly to the case. One of the feedthrough assembly and the case include a feature configured to securely hold the braze and in that the implantable medical device does not include a ferrule.

16 Claims, 11 Drawing Sheets

(51) Int. Cl.
*H02G 3/22* (2006.01)
*A61N 1/375* (2006.01)
*B23K 1/005* (2006.01)

(56) References Cited

U.S. PATENT DOCUMENTS

| | | | |
|---|---|---|---|
| 4,217,137 A | 8/1980 | Kraska et al. |
| 4,315,054 A | 2/1982 | Sack et al. |
| 4,352,951 A | 10/1982 | Kyle |
| 4,354,964 A | 10/1982 | Hing et al. |
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A | 7/1987 | Kraska et al. |
| 4,737,601 A | 4/1988 | Gartzke |
| 4,774,953 A | 10/1988 | Foote |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,333,095 A | 7/1994 | Stevenson et al. |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,769,874 A | 6/1998 | Dahlberg |
| 5,782,891 A | 7/1998 | Hassler et al. |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,870,272 A | 2/1999 | Seifried et al. |
| 5,905,627 A | 5/1999 | Brendel et al. |
| 6,093,476 A | 7/2000 | Horiuchi et al. |
| 6,232,004 B1 | 5/2001 | Lasater |
| 6,275,369 B1 | 8/2001 | Stevenson et al. |
| 6,284,080 B1 | 9/2001 | Haq et al. |
| 6,414,835 B1 | 7/2002 | Wolf et al. |
| 6,490,148 B1 | 12/2002 | Allen et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,765,779 B2 | 7/2004 | Stevenson et al. |
| 6,768,629 B1 | 7/2004 | Allen et al. |
| 6,985,347 B2 | 1/2006 | Stevenson et al. |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,373,965 B2 | 2/2013 | Iyer |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,604,341 B2 | 12/2013 | Barry et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 2001/0013756 A1 | 8/2001 | Mori et al. |
| 2001/0018012 A1 | 8/2001 | Harmand et al. |
| 2001/0041227 A1 | 11/2001 | Hislop |
| 2001/0050837 A1 | 12/2001 | Stevenson et al. |
| 2002/0166739 A1 | 11/2002 | Naerheim |
| 2003/0109903 A1 | 6/2003 | Berrang et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0192578 A1 | 7/2009 | Biggs |
| 2009/0281586 A1 | 11/2009 | Lim |
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0202096 A1 | 8/2010 | Iyer |
| 2010/0241206 A1 | 9/2010 | Truex et al. |
| 2010/0258342 A1 | 10/2010 | Parker |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |

(56) References Cited

U.S. PATENT DOCUMENTS

| | | | |
|---|---|---|---|
| 2012/0006576 A1 | 1/2012 | Barry et al. | |
| 2012/0127627 A1 | 5/2012 | Brendel et al. | |
| 2012/0193117 A1 | 8/2012 | Specht et al. | |
| 2012/0193118 A1 | 8/2012 | Kempf et al. | |
| 2012/0193119 A1 | 8/2012 | Kempf et al. | |
| 2012/0193125 A1 | 8/2012 | Pavlovic et al. | |
| 2012/0193141 A1 | 8/2012 | Reisinger et al. | |
| 2012/0194981 A1 | 8/2012 | Kempf et al. | |
| 2012/0197326 A1 | 8/2012 | Pavlovic | |
| 2012/0197327 A1 | 8/2012 | Specht | |
| 2012/0197335 A1 | 8/2012 | Reisinger | |
| 2012/0197368 A1 | 8/2012 | Reisinger | |
| 2012/0200011 A1 | 8/2012 | Pavlovic | |
| 2012/0203294 A1 | 8/2012 | Troetzschel | |
| 2013/0035733 A1 | 2/2013 | Breyen et al. | |
| 2013/0060312 A1 | 3/2013 | Iyer et al. | |
| 2013/0184796 A1* | 7/2013 | Marzano | A61N 1/3754 607/116 |
| 2013/0184797 A1 | 7/2013 | Tang et al. | |
| 2013/0299233 A1 | 11/2013 | Troetzschel et al. | |
| 2014/0008121 A1 | 1/2014 | Troetzschel et al. | |
| 2014/0144014 A1 | 5/2014 | Troetzschel et al. | |
| 2014/0262494 A1 | 9/2014 | Reisinger et al. | |
| 2014/0345934 A1 | 11/2014 | Markham et al. | |
| 2014/0368298 A1 | 12/2014 | Reisinger | |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| WO | 03073450 | 9/2003 |
| WO | 2004110555 | 12/2004 |
| WO | 2008103166 | 8/2008 |
| WO | 2010091435 | 8/2010 |
| WO | 2013075797 | 5/2013 |

OTHER PUBLICATIONS

Hussain, et al., "Electrical conductivity of an insulator matrix (alumina) and conductor particle (molybdenum) composites", Journal of the European Ceramic Society, vol. 23, Issue 2, Feb. 2003, pp. 315-321.
Gil et al., "Grain Growth Kinetics of Pure Titanium," Scripta Metallurgica et Materialia, vol. 33, No. 8, pp. 1361-1366 (1995).
A partial of the International Search Report for International Application No. PCT/US2014039331 mailed Aug. 29, 2014 (2 pgs.).
The International Search Report and Written Opinion for International Application No. PCT/US2014/039331 mailed Nov. 27, 2014 (16 pgs.).
The Restriction Requirement for U.S. Appl. No. 13/902,287 mailed May 18, 2015 (5 pgs).
The Office Action for U.S. Appl. No. 13/902,287 mailed Dec. 3, 2015 (34 pgs).
The Notice of Allowance for U.S. Appl. No. 13/902,287 mailed May 10, 2016 (6 pgs).

* cited by examiner

CERAMIC FEEDTHROUGH BRAZED TO AN IMPLANTABLE MEDICAL DEVICE HOUSING

CROSS-REFERENCE TO RELATED APPLICATIONS

This application is a divisional of U.S. patent application Ser. No. 13/902,287, entitled "LASER BRAZE CERAMIC TO AN IMPLANTABLE MEDICAL DEVICE HOUSING," having a filing date of May 24, 2013, which is incorporated herein by reference.

BACKGROUND

One aspect relates to a feedthrough device for an implantable medical device. Feedthroughs establish an electrical connection between a hermetically sealed interior and an exterior of the medical device. Known implantable therapeutic devices include cardiac pacemakers or defibrillators, which usually include a hermetically sealed metal housing, which is provided with a connection body, also called header, on one side. Said connection body includes a connection socket for connecting electrode leads. In this context, the connection socket includes electrical contacts that serve to electrically connect electrode leads to the control electronics in the interior of the housing of the implantable therapeutic device—also called implantable device. An essential prerequisite for an electrical bushing of this type is hermetic sealing with respect to the surroundings.

Accordingly, it needs to be made sure that the conducting wires that are introduced into an insulation element and via which the electrical signals proceed, are introduced into the insulation element without any gaps. In this context, it has proven to be disadvantageous that the conducting wires in general are made of a metal and need to be introduced into a ceramic insulation element. In order to ensure long-lasting connection between the two elements, the internal surface of the bore hole in the insulation element must be metallized for soldering the conducting wires into them. Said metallization inside the bore hole in the insulation element has proven to be difficult to apply. Homogeneous metallization of the internal surface of the bore hole in the insulation element can be ensured only by means of expensive procedures. Alternatively or in addition to, brazing may be used to connect the wires to the insulation element. Both metallization and brazing, however, can lead to leaks over time.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment is a method of coupling a feedthrough assembly to a surrounding case of an implantable medical device. The method provides an insulator having a plurality of conducting elements extending therethrough. The insulator with conducting elements is placed within an opening of a case, thereby defining a narrow space between the insulator and the case. A braze preform is placed adjacent the insulator and case in the narrow space. The insulator is heated with a laser until the temperature of the adjacent preform is raised above its melting point such that it flows and fills the space between the insulator and the case.

In one embodiment, the temperature of the preform is raised above its melting point by directing the laser exclusively at the case and the insulator and not at the preform. In this way, by avoiding directing too much energy at the preforms, this creates a high-quality seal between the feedthrough assembly and the case with the melted preform. If the laser were to be directed at the preform, spattering of the material of the preforms will occur, such that the seal between the case and feedthrough assembly can be compromised.

In one embodiment, the braze preform is place on a feature that is formed in the case or in the insulator, or in their combination. In one embodiment, the feature is configured with a surface configured to securely hold the braze preform while it is heated by the laser. In this way, the preform will stay in the correct position between the case and in the insulator so that its melting will fill the narrow space therebetween.

In one embodiment, the braze preform, the insulator, and the case are first heated in an oven or other heating apparatus prior to heating the insulator with the laser. In this way, the heat from the laser does not need to increase the temperature of the preform from room temperature all the way up to its melting point, which would require significant laser energy and could cause defects in some instances. For example, if the laser is used to increase the temperature all the way from room temperature to the melting point of the preform, the insulator at which the laser is directed may experience surface damage and cracking. In one embodiment, the braze preform, the insulator, and the case are heated to at least 600-800° C. prior to heating the insulator with the laser. In that case, the heat from the laser only needs to increase the temperature of the preforms from 600-800° C. to the melting temperature of the preforms.

In one embodiment, the braze preform, the insulator, and the case are heated in a container, which is vacuum-sealed, prior to heating the insulator with the laser. In one embodiment, the container is filled with an inert gas while heating the braze preform, the insulator, and the case in the container. In one embodiment, it is advantageous to leave the braze preform, the insulator, and the case in the container even after it is heater therein, and then heating the insulator with a laser through a glass portion of the container while the insulator is within the container. In one embodiment, the vacuum-sealed and/or inert gas-filled container prevents oxidation of the case during heating.

In one embodiment, the insulator is heated with a laser on a surface opposite where the braze preform is placed, such that the braze preform is pulled toward the laser as it melts from the heat of the applied laser. In some cases this will help pull the molten braze through the narrow space between the insulator and the case ensuring a filled and hermetic seal between them.

In one embodiment, an implantable medical device includes a feedthrough assembly comprising an insulator and a plurality of conducting elements extending therethrough. A case is provided with an opening into which the feedthrough assembly is placed defining a narrow space therebetween. A braze material fills the narrow space, thereby hermetically sealing the feedthrough assembly to the case. The medical device is characterized in that one of the feedthrough assembly and the case comprise a feature configured to securely hold the braze and in that the implantable medical device does not include a ferrule. In one embodiment, the feature is a step in the case or feedthrough assembly defining a surface on which the braze material is securely held. In this way, the preform will stay in the correct position between the case and in the insulator so that its melting will fill the narrow space therebetween.

In one embodiment, the feedthrough assembly comprises a top surface that is exterior to the case and the step has a surface that is parallel to the top surface of the feedthrough assembly. This surface in the step provides an ideal flat surface on which the preform can sit, without sliding or moving, so that it can be melted into place. In one embodiment, the narrow space between the feedthrough assembly and case is no less than 10 μm and no more than 50 μm. This distance range provides a good capillary action for the braze to fill the space and provide a good seal.

In one embodiment, the insulator and plurality of conducting elements are hermetically sealed together without solder or braze. In this way, the hermetic seal between the insulator and plurality of conducting elements is not compromised during the melting of the braze between the feedthrough assembly and case. In one embodiment, this is achieved by using cermet for the plurality of conducting elements.

In one embodiment, the medical device is characterized in that the feedthrough assembly includes metallization on at least one surface in order to control the dimensions of the braze. In one embodiment, it is advantageous for the metallization on the feedthrough assembly to control the braze dimensions such that it is at least 0.010 inches below the top surface of the feedthrough assembly and at least 0.010 inches above a bottom surface of the feedthrough assembly.

Figure 1A:
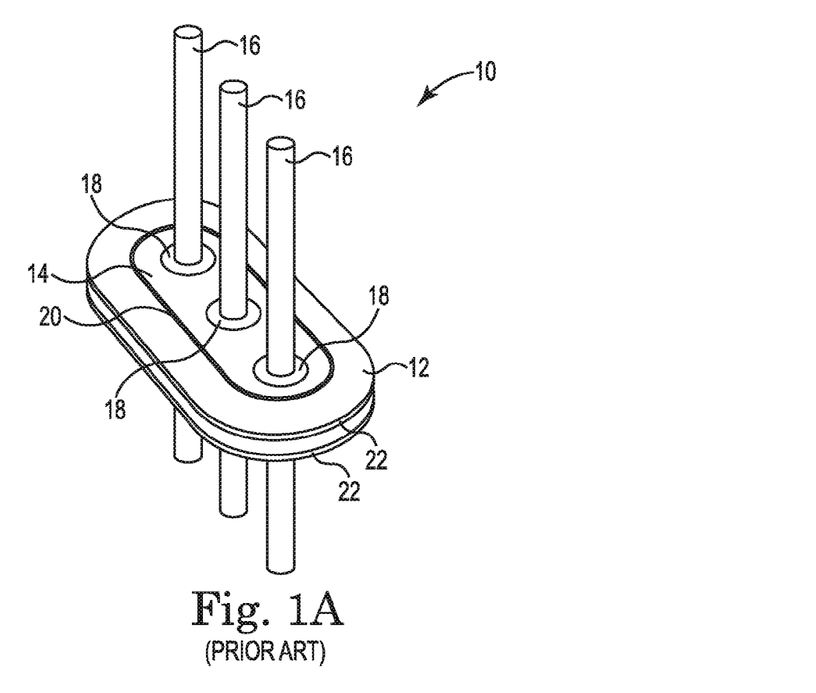
FIGS. 1A and 1B illustrate a feedthrough device in accordance with the prior art.
Figure 1B:
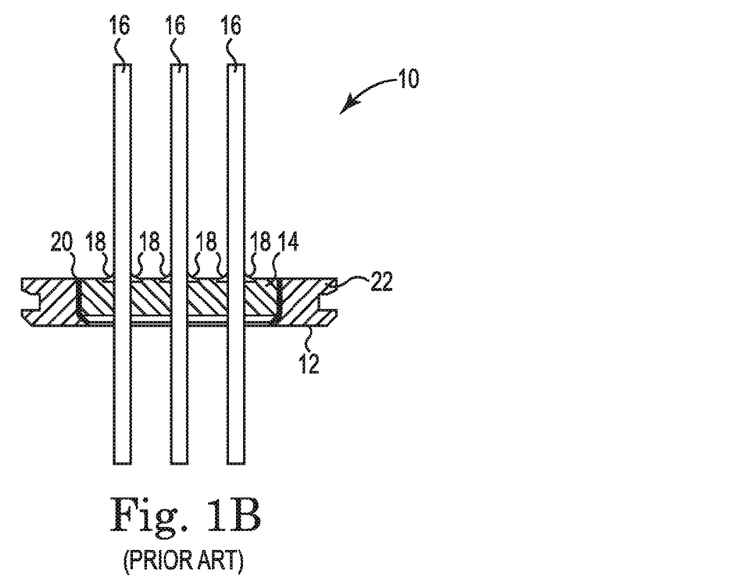

FIGS. 1A and 1B illustrate respective perspective and sectional views of feedthrough device 10, such as for an implantable medical device, in accordance with the prior art. Feedthrough device 10 includes ferrule 12, insulator 14 and feedthrough pins 16. Ferrule 12 is a frame-like structure with an internal opening into which insulator 14 is formed and through which feedthrough pins 16 extend. Insulator 14 facilitates feedthrough pins 16 extending through the frame-like structure of ferrule 12 in a non-conductive manner.

Ferrule 12 is configured to fit into an opening of a case for an implantable medical device and such that it can be tightly secured thereto in order to ensure a hermetic seal with respect to an internal space of the medical device. Feedthrough pins 16 extend from within the internal space of the case of the medical device to outside the device, thereby providing electrical connection from the inside to the outside, while maintaining a hermetic seal. Flanges 22 can be provided on ferrule 12 to further aid in securing feedthrough device 10 to the opening of the case of the implantable medical device and ensuring its hermetic seal.

Typically, insulator 14 is a ceramic or glass material, while ferrule 12 is metallic. Ferrule 12 is metallic so that it can be readily welded to a metallic case of the implantable medical device. In order for the ceramic material of insulator 14 to be coupled to the metallic material of ferrule 12, insulator 14 is typically "metalized" with metalized coating 20. Alternatively, a metallic braze is used to secure ceramic material of insulator 14 to the metallic material of ferrule 12. Similarly, braze 18 is used to couple the ceramic material of insulator 14 to feedthrough pins 16, which are metallic conductors.

Use of braze 18 to secure insulator 14 to feedthrough pins 16 and to secure insulator 14 to ferrule 12, and/or the need for metalized coating 20 to secure insulator 14 to ferrule 12 creates extra processing steps and adds to the complication and expense of manufacturing feedthrough device 10. Such braze 18 and metallization 20 can also lead to leaks and failure of a hermitic seal for feedthrough device 10.

Figure 2:
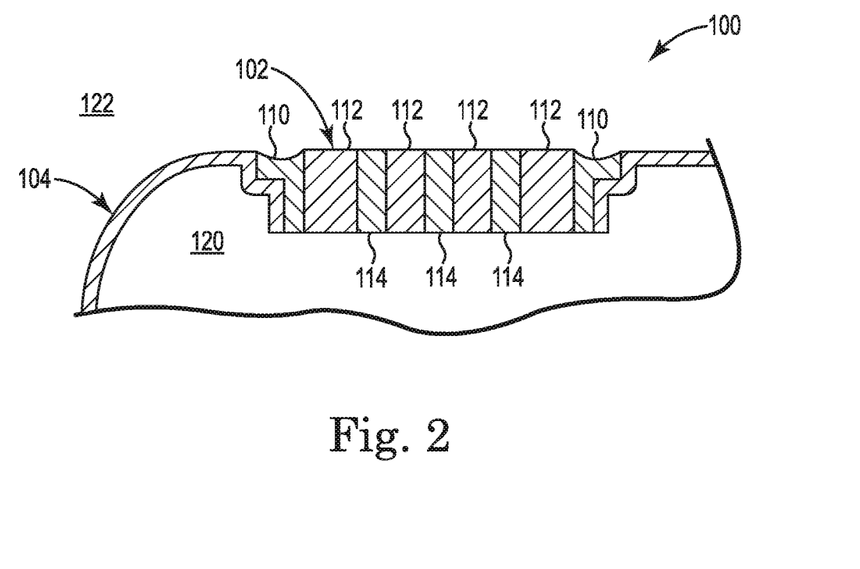
FIG. 2 illustrates a cross-sectional view of a feedthrough assembly in an implantable medical device in accordance with one embodiment.

FIG. 2 illustrates implantable medical device 100 in accordance with one embodiment. Implantable medical device 100 includes feedthrough assembly 102 and case 104. Feedthrough assembly 102 includes insulator 112 and conducting elements 114. In one embodiment, braze 110 is added between feedthrough assembly 102 and case 104 in order to secure and seal feedthrough assembly 102 to case 104. In one embodiment, feedthrough assembly 102 is sealed to case 104, such that an interior 120 of case 104 is hermetically sealed relative to its exterior 122, without the use of a ferrule.

In one embodiment, conducting elements 114 of feedthrough assembly 102 are an electrically conductive material such that they provide a conductive path from internal space 120 to external space 122 of case 104. Insulator 112 is of a non-electrically conductive material such that there is no conductive connection among the conducting elements 114 or between the conducting elements 114 and case 104. All of the interfaces between insulator 112 and conducting elements 114 and between insulator 112 and case 104 are sealed in such a way that a hermetic seal is maintained between internal space 120 and external space 122 of case 104. In one embodiment, all of the interfaces between insulator 112 and conducting elements 114 are hermetically sealed without the use of braze or solder, as will be more fully explained below.

Unlike feedthrough device 10 of FIG. 1, implantable medical device 100 in accordance with the exemplary embodiment of FIG. 2 has no ferrule. Whereas ferrule 12 of feedthrough device 10 is metallic an easily welded to a case, feedthrough assembly 102 has no ferrule and is instead directly coupled to case 104 using braze 110 as will be discussed more fully below.

In one embodiment, feedthrough assembly 102 is assembled by forming insulator 112 and conducting elements 114 in a first process. In one embodiment, insulator 112 is a ceramic material, such as aluminum oxide (Al2O3), and conducting elements 114 are a cermet material.

In the context of one embodiment, the terms, "cermet" or "cermet-containing," shall refer to all composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or the cermet-containing elements proceeds just like with homogeneous powders with the exception that the metal is compacted more strongly at the same pressuring force as compared to the ceramic material. The cermet-containing bearing element has a higher thermal shock and oxidation resistance than sintered hard metals. In most cases, the ceramic components of the cermet are aluminum oxide (Al2O3) and zirconium dioxide (ZrO2), whereas niobium, molybdenum, titanium, cobalt, zirconium, chromium and platinum are conceivable as metallic components.

The ceramic of insulator 112 can be, for example, a multi-layer ceramic sheet into which a plurality of vias is introduced. The cermet of conducting elements 114 is then introduced into the vias. In one embodiment, both materials are introduced in a green state, and as such, the combination is fired together. Accordingly, the joining of the insulator 112 and conducting elements 114 forms a hermetic seal therebetween without the use of braze or solder.

Figure 3A:
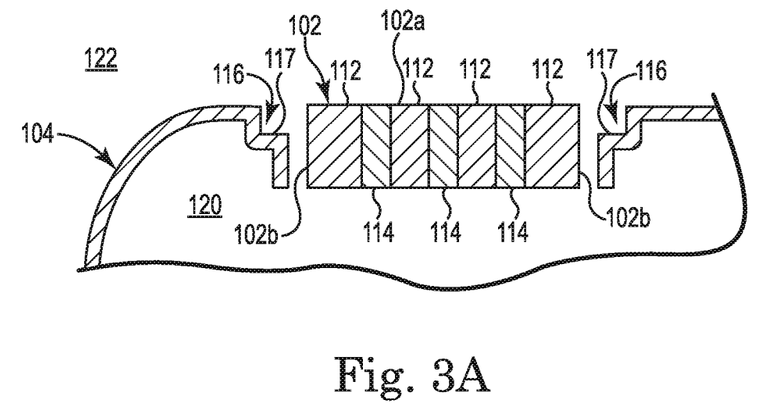
FIGS. 3A-3C illustrate cross-sectional views of a feedthrough assembly partially assembled into an implantable medical device in accordance with one embodiment.

FIGS. 3A-3D illustrate cross sectional views illustrating one process to secure feedthrough assembly 102 to case 104 in accordance with one embodiment. FIG. 3A illustrates feedthrough assembly 102 placed within an opening of case 104 in preparation for securing feedthrough assembly 102 to case 104 in accordance with one embodiment. In one embodiment, case 104 is provided with features 116 adjacent the outside surface 102b of feedthrough 102. In one example, the feature is a step or jog in case 104 that defines a seating surface 117, which is substantially parallel to a top surface 102a of feedthrough 102.

Figure 3B:
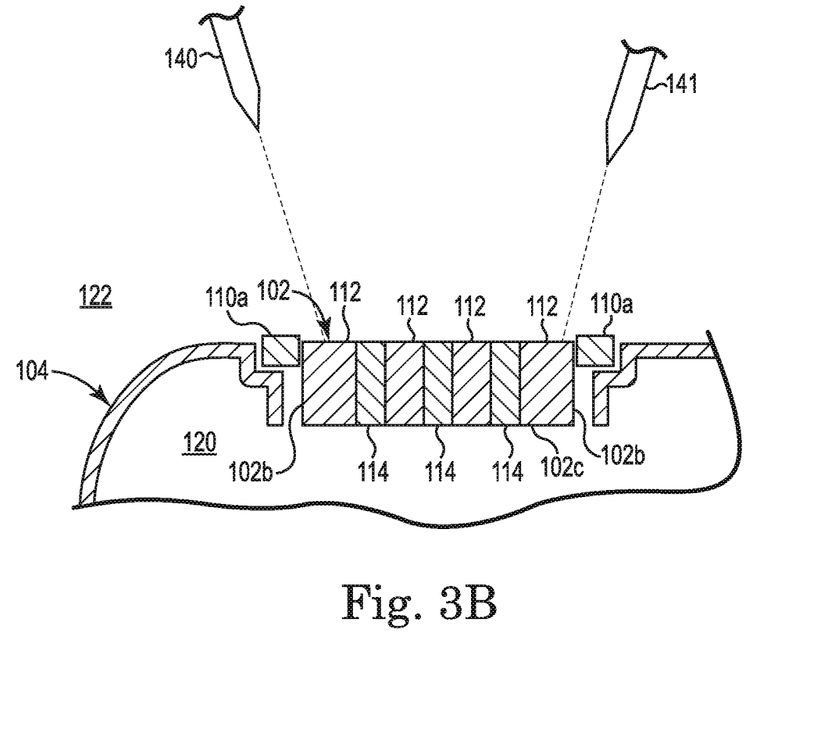

FIG. 3B illustrates feedthrough assembly 102 placed within an opening of case 104 in a further step of securing feedthrough assembly 102 to case 104 in accordance with one embodiment. Here, preforms 110a are placed between the outside surface 102b and case 104. In one example, preforms 110a are placed on features 116 so that they are steadily secured for the further process. For example, preforms 110a may be placed on seating surface 117. Once preforms 110a are in place, lasers 140 and 141 are directed at feedthrough 102 and activated. In one embodiment, lasers 140 and 141 are scanned across insulator 112, and particularly toward outside surface 102b, in order to heat up the ceramic in that area. In addition, preforms 110a are placed so that they are closely proximate to the outside surface 102b of feedthrough 102. As such, preforms 110a will begin to heat up from the adjacent heat from insulator 112.

In one embodiment, preforms 110a are gold braze placed relatively close to outside surface 102b of feedthrough 102. In one embodiment, lasers 140 and 141 heat feedthrough 102 to a temperature high enough so as to induce a temperature in preforms 110a above the melting point of gold. As such, preforms 110a will begin to melt and flow from the high temperature caused by activated lasers 140 and 141.

In one embodiment, two lasers 140 and 141 are used, but in other embodiments a single laser is used. In yet other embodiments, additional lasers are used to heat feedthrough 102. In some embodiments, the lasers are directed toward outside surface 102b to ensure it is heated and will therefore transfer heat effectively to preforms 110a. In other embodiments, lasers 140 and 141 scan the entire top surface of feedthrough 102 to heat the entire feedthrough 102. In yet other embodiments, lasers 140 and 141 scan the entire device, including case 104, preforms 110a, and feedthrough assembly 102. In most instances, however, lasers 140 and 141 are not directed exclusively at preforms 110a, because if too much energy is focused directly at preforms 110a spattering of the material of preforms 110a will occur. In that situation, the seal between case 104 and feedthrough assembly 102 can be compromised.

Furthermore, although lasers 140 and 141 are illustrated "above" (relative to how illustrated in FIG. 3B) top surface 102a of feedthrough 102, they can also be located "below" feedthrough 102 such that they would be directed at lower surface 102c of feedthrough 102. In one embodiment, directing lasers at the lower surface 102c aids in drawing the melted material of preforms 110a toward the laser, thereby filling the space defined between outside surface 102b of feedthrough 102 and the adjacent portions of case 104.

Figure 3C:
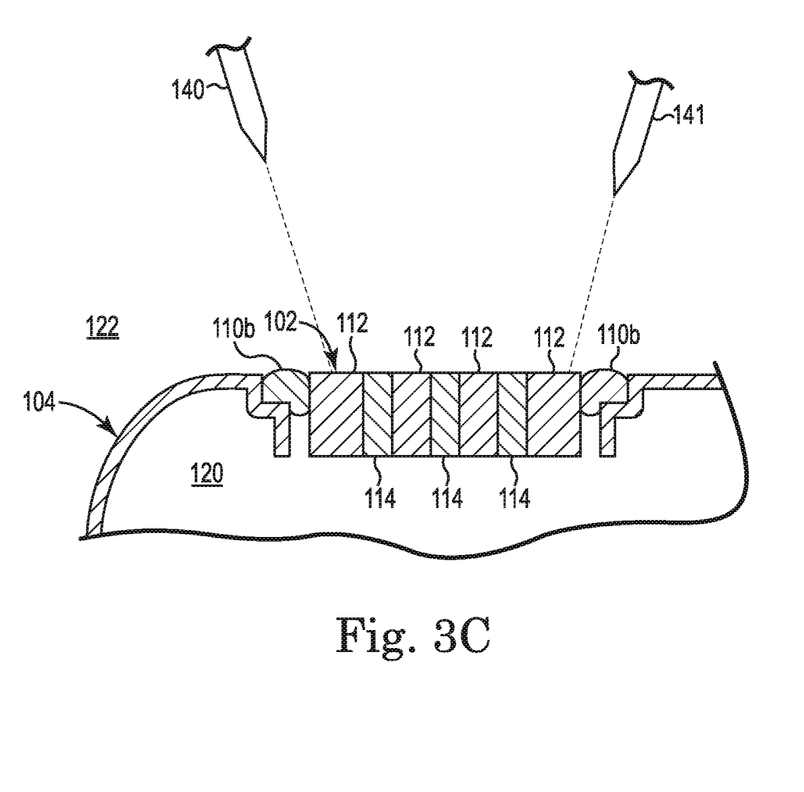

FIG. 3C illustrates feedthrough assembly 102 placed within case 104 in a further step of securing feedthrough assembly 102 to case 104 in accordance with one embodiment. Here, molten preforms 110b are illustrated flowing in the space between outside surface 102b of feedthrough 102 and case 104, having been subjected to heat of feedthrough assembly 102 that was produced by lasers 140 and 141. As heat continues to be produced from the lasers directed at feedthrough assembly 102, molten preforms 110b flow and fill the space between feedthrough 102 and case 104.

In one embodiment, the space defined between outside surface 102b of feedthrough 102 and the adjacent portions of case 104 is controlled such that it remains relatively narrow in order to encourage good capillary action of molten preforms 110b. In one embodiment, the space between outside surface 102b of feedthrough 102 and the adjacent portions of case 104 is maintained between 10-50 µm. Where molten preforms 110b are a gold braze, this distance range provides a good capillary action for the braze to fill the space.

In one embodiment, lasers 140 and 141 are $CO_2$ lasers controlled to heat the ceramic of insulator 112 to a high temperature above the melting point of preforms 110a. In one example, where preforms are gold braze, the lasers heat the insulator 112 well above the melting point of gold, that is, well above 1,064° C. In one embodiment, both the feedthrough assembly 102 and case 104 are preheated before application of laser energy from lasers 140 and 141, such as for example, in an oven. In one example, feedthrough assembly 102 and case 104 are preheated to a temperature of 600-800° C. before application of energy from lasers 140 and 141. In this way, less heating energy is needed from lasers 140 and 141 to melt preforms 110a. In some cases, if lasers 140 and 141 are used without first preheating in order to melt preforms 110a, such as all the way from room temperature, surface damage to insulators 112 can result because the energy needed from lasers 140 and 141 is much greater to maintain a high temperature to melt preforms 110a.

In one embodiment, feedthrough assembly 102, case 104 and preforms 110a are heated in a vacuum or in an inert gas. For example, feedthrough assembly 102, case 104 and preforms 110a are heated in argon gas in order to prevent oxidation of case 104, which is in one example, titanium. In one embodiment, feedthrough assembly 102, case 104 and preforms 110a are maintained in the vacuum or inert gas even during laser heating from lasers 140 and 141. In one embodiment, a vacuum/gas controlled sealed container or box is provided for heating feedthrough assembly 102, case 104 and preforms 110a. In one example, the box includes a window through which lasers 140 and 141 are directed in order to transmit light through to the feedthrough assembly 102, case 104 and/or preforms 110a.

Because conducting elements 114 are cermet embedded adjacent ceramic insulator 112, a hermetic seal therebetween is established without the use of braze or solder. In one embodiment, this assures that even where the entire feedthrough assembly 102 is heated to high temperatures, there is no concern of braze or solder reflowing, as there would be for conventional feedthrough assemblies (such as in FIGS. 1A-1B) that must use braze of solder to achieve a hermitic seal between conductors and insulator. In the case of these prior feedthrough assemblies, heating with lasers 140 and 141 would very likely reflow the braze or solder that secures the insulator 14 to the feedthrough pins 16, thereby jeopardizing the hermetic seal.

Figure 3D:
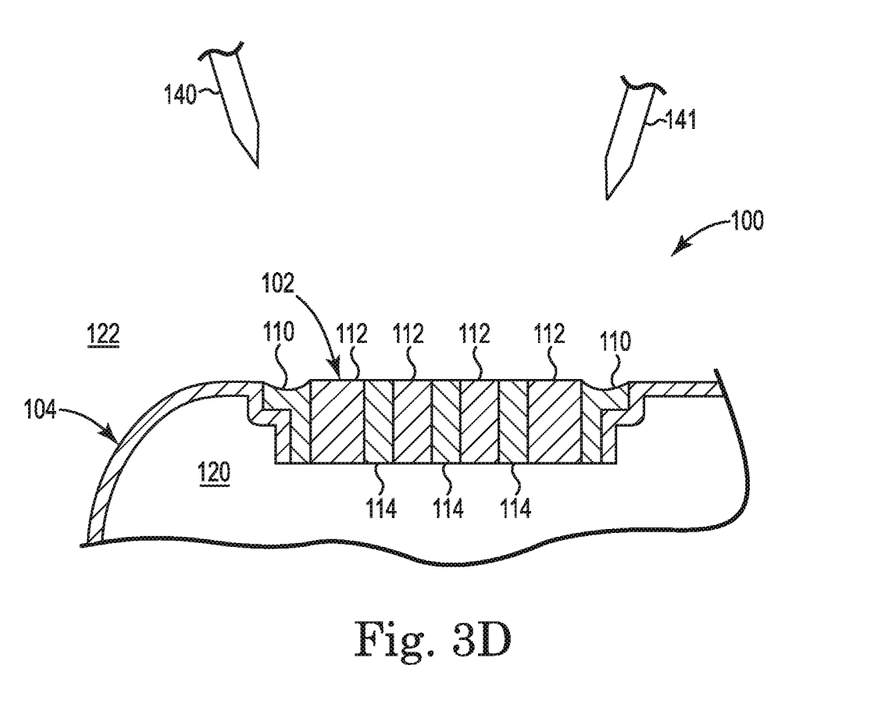
FIG. 3D illustrates a cross-sectional view of a feedthrough assembly assembled into an implantable medical device in accordance with one embodiment.
Figure 4:
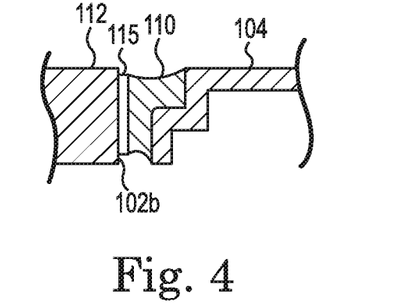
FIG. 4 illustrates a partial cross-sectional view of a feedthrough assembly in an implantable medical device in accordance with one embodiment.

FIG. 3D illustrates implantable medical device 100 including feedthrough assembly 102 secured within case 104 in accordance with one embodiment. Here, molten preforms 110b have solidified as energy from lasers 140 and 141 have been discontinued, thereby ending the heating of feedthrough assembly and allowing braze 110 to solidify as it cools. In this way, implantable medical device 100 has feedthrough assembly 102 hermetically sealed directly to case 104 without requiring a ferrule, such as was needed for prior designs, such as feedthrough device 10 of FIGS. 1A-1B In one embodiment, braze 110 is controlled relative to feedthrough assembly 102 and case 104 in order to optimize its final configuration. FIG. 4 illustrates a portion of feedthrough assembly 102, specifically the area between outside surface 102b of feedthrough assembly 102 and case 104. Here, a portion of outside surface 102b, along the surface of insulator 112, includes metallization 115. In one embodiment, metallization 115 is applied before preforms 110a are inserted and melted. Metalizing outer surface 102b allows molten preforms 110b to "wet" to outer surface 102b.

In addition, in one embodiment, metallization 115 acts as a braze stop, so as to control the flow of molten preforms 110b. By positioning metallization 115 in the desired locations, the final position of braze 110 is controlled, including where braze 110 will stop, thereby defining the final dimensions of braze 110.

In this way, in one embodiment metallization 115 is stepped back slightly from the top and bottom surfaces 102a and 102c of feedthrough assembly 102 such that braze 110 will accordingly also be slightly offset. In one embodiment, metallization 115, and accordingly braze 110, is controlled to be 0.010 inches below the top surface 102a of feedthrough assembly 102 and 0.010 inches above the bottom surface 102c of feedthrough assembly 102. In one embodiment, this offset forms a superior seal between feedthrough assembly 102 and case 104.

Figure 5:
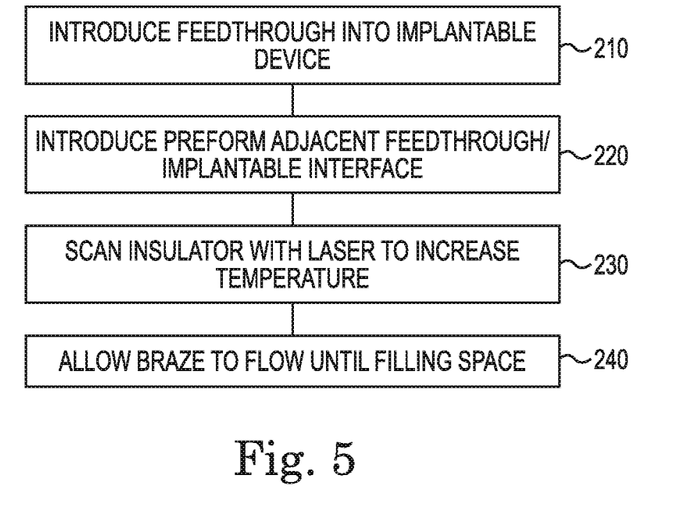
FIG. 5 illustrates a flow diagram of a method of forming a feedthrough assembly in accordance with one embodiment.

FIG. 5 is a flow diagram illustrating a process 200 of making a feedthrough assembly in accordance with one embodiment. In a first step 210, a feedthrough assembly is introduced into a case of an implantable medical device. In one embodiment, a relatively small space is left between the feedthrough assembly and the case. At step 220, a preform is introduced into the small space between the feedthrough assembly and the case. In one embodiment, either the case or the feedthrough assembly, or their combination, have a feature on which the preform can be placed in a secure manner.

At step 230, a laser is scanned over the surface of the insulator of the feedthrough assembly in order to bring up the temperature of the insulator. In one embodiment, the insulator is immediately adjacent the preform such that heating the insulator also heats the preform. In one embodiment, the laser is controlled to heat the ceramic a temperature above the melting point of the preforms. In one embodiment, where preforms are gold braze, the laser heat the insulator well above 1,064° C. In one embodiment, each of the feedthrough assembly, the case and the preform are first preheated before application of laser energy. In one example, the feedthrough assembly, case and preform are preheated to a temperature of 600-800° C. before application of energy from the laser.

At step 240, the laser continues to heat the feedthrough assembly, and in some instances the case and preform as well, such that the preform flows into the space between the feedthrough assembly and case. Once the space is filled, the laser is deactivated such that the molten preform solidifies thereby securing the feedthrough assembly to the case.

Figure 6A:
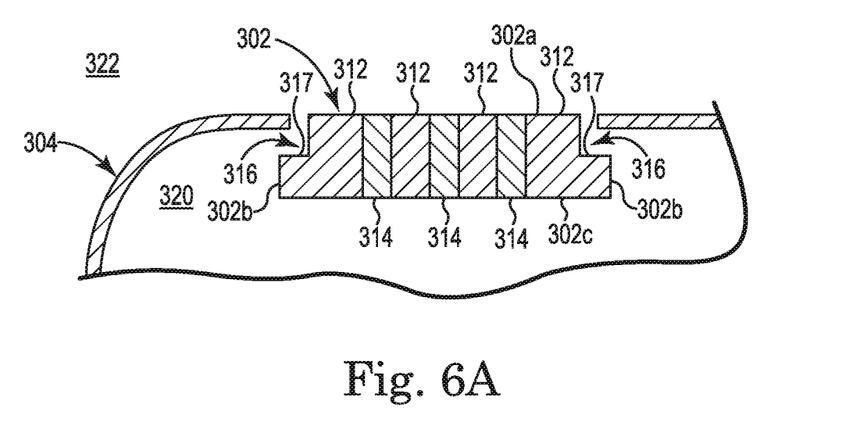
FIG. 6A illustrates a feedthrough assembly and an implantable medical device in accordance with one embodiment.
Figure 6B:
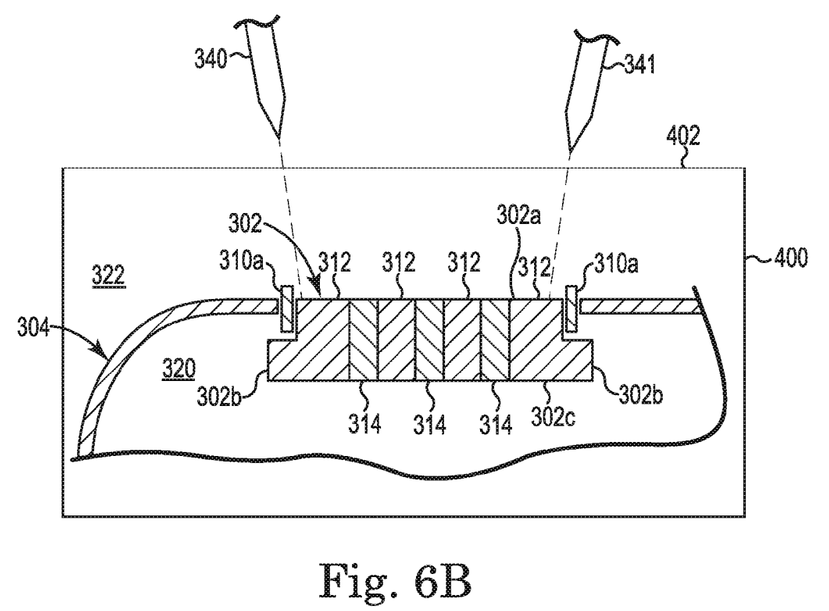
FIG. 6B illustrates a cross-sectional view of a feedthrough assembly partially assembled into an implantable medical device in accordance with one embodiment.
Figure 6C:
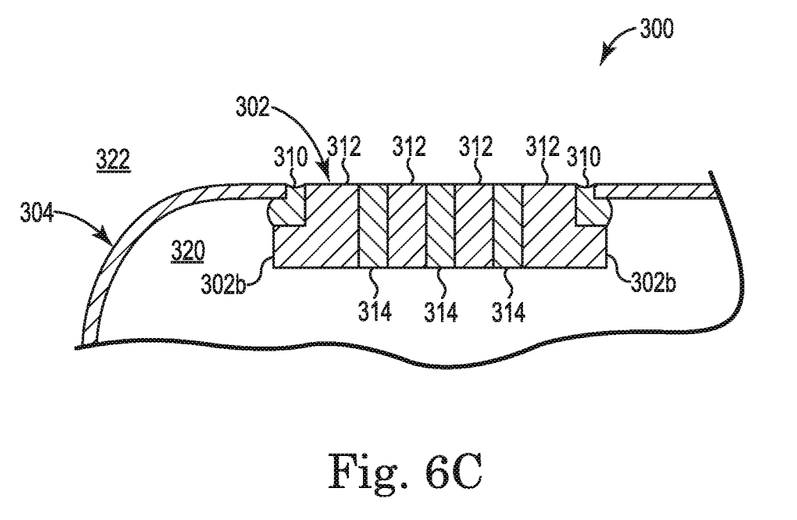
FIG. 6C illustrates a cross-sectional view of a feedthrough assembly in an implantable medical device in accordance with one embodiment.

FIGS. 6A-6C illustrate cross sectional views illustrating one process to secure feedthrough assembly 302 to case 304 in accordance with one embodiment. FIG. 6A illustrates feedthrough assembly 302 placed within an opening of case 304 in preparation for securing feedthrough assembly 302 to case 304 in accordance with one embodiment. In one embodiment, feedthrough assembly 302 is provided with features 316 on the outside surface 302b of feedthrough 302. In one example, the feature 316 is a step or jog in feedthrough assembly 302 that defines a seating surface 317, which is substantially parallel to a top surface 302a of feedthrough 302.

FIG. 6B illustrates feedthrough assembly 302 placed within an opening of case 304 in a further step of securing feedthrough assembly 302 to case 304 in accordance with one embodiment. In one embodiment, preforms 310a are placed between the outside surface 302b and case 304. In one example, preforms 310a are placed on features 316 so that they are steadily secured for the further process. For example, preforms 310a may be placed on seating surface 317.

In one embodiment, feedthrough assembly 302, case 304, and preforms 310a are all secured and heated in sealed container 400. In one example, container 400 is vacuum-sealed and in another it is filled with an inert gas, such as argon. In one embodiment, container 400 includes window 402 through which lasers 340 and 341 are directed to heat feedthrough assembly 302, case 304 and/or preforms 310a. Once preforms 310a are in place, lasers 340 and 341 are directed at feedthrough 302 and activated. In one embodiment, lasers 340 and 341 are scanned across insulator 312, and particularly toward outside surface 302b, in order to heat up the ceramic in that area. In addition, preforms 310a are placed so that they are closely proximate to the outside surface 302b of feedthrough 302. As such, preforms 310a will begin to heat up from the adjacent heat from insulator 312.

In one embodiment, preforms 310a are gold braze placed relatively close to outside surface 302b of feedthrough 302. In one embodiment, lasers 340 and 341 heat feedthrough 302 to a temperature high enough so as to induce a temperature in preforms 310a above the melting point of gold. As such, preforms 310a will begin to melt and flow from the high temperature.

As with the embodiment described above, a single laser, or two or more lasers may be used. Also, the lasers can be directed toward outside surface 302b or can scan the entire top surface of feedthrough 302. Similarly to the previous embodiment, lasers can be directed at top surface 302b or directed at lower surface 302c of feedthrough 302.

FIG. 6C illustrates implantable medical device 300 including feedthrough assembly 302 secured within case 304 in accordance with one embodiment. Here, molten preforms 310b have solidified as energy from lasers 340 and 341 have been discontinued, thereby ending the heating of feedthrough assembly 302 and allowing braze 310 to solidify as it cools. In this way, implantable medical device 300 has feedthrough assembly 302 hermetically sealed directly to case 304 such that an interior 320 of case 304 is hermetically sealed relative to its exterior 322, without requiring a ferrule as is needed for prior designs like feedthrough device 10 of FIGS. 1A-1B. Attaching feedthrough assembly 302 directly to case 304 without the need of a ferrule simplifies the assembly process and steps, reduces parts and material, and reduces overall time and cost.

In one embodiment, implantable medical device 100 of FIG. 2 includes case 104 having feature 116 useful for holding preform 110a, while implantable medical device 300 of FIG. 6C includes feedthrough assembly 302 having feature 316 useful for holding preform 310a. In yet other embodiments, both the case and feedthrough assemblies can include features, or their combinations define features, that are able to hold preforms, which can then be subsequently heated and melted to form a braze that will hermetically seal the feedthrough assembly to the case.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An implantable medical device comprising:
a feedthrough assembly comprising an insulator and a plurality of conducting elements extending therethrough;
a case with an opening into which the feedthrough assembly is positioned defining a narrow space therebetween;
a braze material filling the narrow space, thereby hermetically sealing the feedthrough assembly to the case;
characterized in that the case comprises a step configured to securely hold the braze and in that the implantable medical device does not include a ferrule.

2. The implantable medical device of claim 1, wherein the feedthrough assembly comprises a top surface that is exterior to the case and the step has a surface that is parallel to the top surface of the feedthrough assembly.

3. The implantable medical device of claim 1, wherein the narrow space is no less than 10μm and no more than 50 μm.

4. The implantable medical device of claim 1, wherein the insulator and plurality of conducting elements are hermetically sealed together without solder or braze.

5. The implantable medical device of claim 4, wherein the plurality of conducting elements comprise cermet.

6. The implantable medical device of claim 4, characterized in that the feedthrough assembly includes metallization on at least one surface to control the dimensions of the braze.

7. The implantable medical device of claim 6, wherein the metallization on the feedthrough assembly controls the braze such that it is at least 0.010 inches below the top surface of the feedthrough assembly and at least 0.010 inches above a bottom surface of the feedthrough assembly.

8. An implantable medical device comprising:
a feedthrough assembly comprising an insulator and a plurality of conducting elements extending therethrough;
a case with an opening into which the feedthrough assembly is positioned defining a narrow space therebetween;
a braze material filling the narrow space, thereby hermetically sealing the feedthrough assembly to the case;
characterized in that one of the feedthrough assembly and the case comprise a step configured to securely hold the braze and in that the implantable medical device does not include a ferrule.

9. The implantable medical device of claim 8, wherein the feature is a step in the case defining a surface against which the braze material is securely held.

10. The implantable medical device of claim 8, wherein the feature is a step in the feedthrough assembly defining a surface against which the braze material is securely held.

11. The implantable medical device of claim 9, wherein the feedthrough assembly comprises a top surface that is exterior to the case and the step has a surface that is parallel to the top surface of the feedthrough assembly.

12. The implantable medical device of claim 8, wherein the narrow space is no less than 10μm and no more than 50 μm.

13. The implantable medical device of claim 8, wherein the insulator and plurality of conducting elements are hermetically sealed together without solder or braze.

14. The implantable medical device of claim 13, wherein the plurality of conducting elements comprise cermet.

15. The implantable medical device of claim 13, characterized in that the feedthrough assembly includes metallization on at least one surface to control the dimensions of the braze.

16. The implantable medical device of claim 13, wherein the metallization on the feedthrough assembly controls the braze such that it is at least 0.010 inches below the top surface of the feedthrough assembly and at least 0.010 inches above a bottom surface of the feedthrough assembly.

* * * * *